US009070486B2

(12) United States Patent
Guerrera et al.

(10) Patent No.: US 9,070,486 B2

(45) Date of Patent: Jun. 30, 2015

(54) RADIATION SHIELDING COCKPIT CARRYING AN ARTICULATED ROBOTIC ARM

(71) Applicant: Corindus, Inc., Waltham, MA (US)

(72) Inventors: Stephen Guerrera, Holliston, MA (US); Robert Elden, Cambridge, MA (US)

(73) Assignee: Corindus Inc., Waltham, MA (US)

( * ) Notice: Subject to any disclaimer, the term of this patent is extended or adjusted under 35 U.S.C. 154(b) by 0 days.

(21) Appl. No.: 14/212,143

(22) Filed: Mar. 14, 2014

(65) Prior Publication Data

US 2014/0264095 A1 Sep. 18, 2014

Related U.S. Application Data

(60) Provisional application No. 61/791,707, filed on Mar. 15, 2013.

(51) Int. Cl.

| | |
|---|---|
| ***A61B 19/00*** | (2006.01) |
| ***G21F 7/02*** | (2006.01) |
| ***G21F 3/02*** | (2006.01) |
| ***G21F 3/00*** | (2006.01) |
| ***G21F 7/06*** | (2006.01) |

(52) U.S. Cl.

CPC ... *G21F 3/00* (2013.01); *G21F 7/06* (2013.01)

(58) Field of Classification Search

CPC ............... A61N 5/10; G21F 3/00; G21F 7/06; A61B 6/107; A61B 6/548

USPC .................. 250/515.1, 517.1, 505.1, 455.11; 600/435, 434, 119

See application file for complete search history.

(56) References Cited

U.S. PATENT DOCUMENTS

| | | | | |
|---|---|---|---|---|
| 6,726,675 | B1 | 4/2004 | Beyar | |
| 7,887,549 | B2 | 2/2011 | Wenderow et al. | |
| 8,382,372 | B2 * | 2/2013 | Maschke | 378/209 |
| 8,399,871 | B2 | 3/2013 | Beyar et al. | |
| 2009/0046146 | A1 * | 2/2009 | Hoyt | 348/143 |
| 2011/0174997 | A1 * | 7/2011 | Rees | 250/516.1 |
| 2012/0179167 | A1 * | 7/2012 | Wenderow et al. | 606/130 |
| 2014/0284503 | A1 * | 9/2014 | Stevick et al. | 250/515.1 |

* cited by examiner

*Primary Examiner* — Nikita Wells

(74) *Attorney, Agent, or Firm* — Rathe Lindenbaum LLP

(57) ABSTRACT

A radiation shielded cockpit comprises a radiation blocking material which creates a semi-enclosed work space and which is provided with a structure for receiving and supporting an articulated robot arm and an articulated robot arm that engages the supporting structure in a readily removable manner.

20 Claims, 1 Drawing Sheet

RADIATION SHIELDING COCKPIT CARRYING AN ARTICULATED ROBOTIC ARM

CROSS-REFERENCE TO RELATED PATENT APPLICATIONS

This application claims priority to U.S. Provisional Application No. 61/791,707 entitled RADIATION SHIELDING COCKPIT WITH ARTICULATED ROBOTIC ARM filed Mar. 15, 2013 and incorporated herein by reference in its entirety.

BACKGROUND

There are systems for the performance of medical procedures in which a percutaneous device is inserted into a human patient with the guidance of an X-ray image using a mechanism held adjacent to the patient by a robotic arm and the mechanism is controlled from a remote cockpit which provides shielding to the operator of the system from the radiation generated in obtaining the X-ray image. The arm has typically been attached to the patient table by a rail and removed from the rail and placed on the floor between procedures.

SUMMARY

The radiation shielding cockpit from which a robotic catheter procedure system may be controlled is provided with a structure to which an articulated robotic arm may be attached. The arm may be statically attached simply to store it between catheter procedures or it may be dynamically attached such that it may participate in a robotic catheter procedure. In the latter case a sensing and signaling mechanism is provided which senses changes in the location of the patient table which supports the patient who is to undergo a robotic catheter procedure involving the articulated robotic arm.

One embodiment involves a radiation shielded cockpit comprising a radiation blocking material which creates a semi-enclosed work space is provided with a structure for receiving and supporting an articulated robot arm and an articulated robot arm that engages the supporting structure in a readily removable manner.

One embodiment involves a radiation shielded cockpit comprising a configuration of radiation blocking materials which creates a semi-enclosed work space is provided with a structure for receiving and supporting an articulated robot arm and an articulated robot arm that engages the supporting structure and has a mechanism for tracking the horizontal movement of a patient table and moving the robot arm in accordance with that tracking One embodiment involves a process for storing an articulated robot arm by providing the articulated robot arm, a configuration of radiation blocking materials which creates a semi-enclosed work space and a structure that is attached to the configuration of radiation blocking materials and engages the articulated robot arm in a readily removable manner and when so engaged supports the arm and causing the structure to engage the robot arm in readily removable manner.

DETAILED DESCRIPTION

Figure 1A:
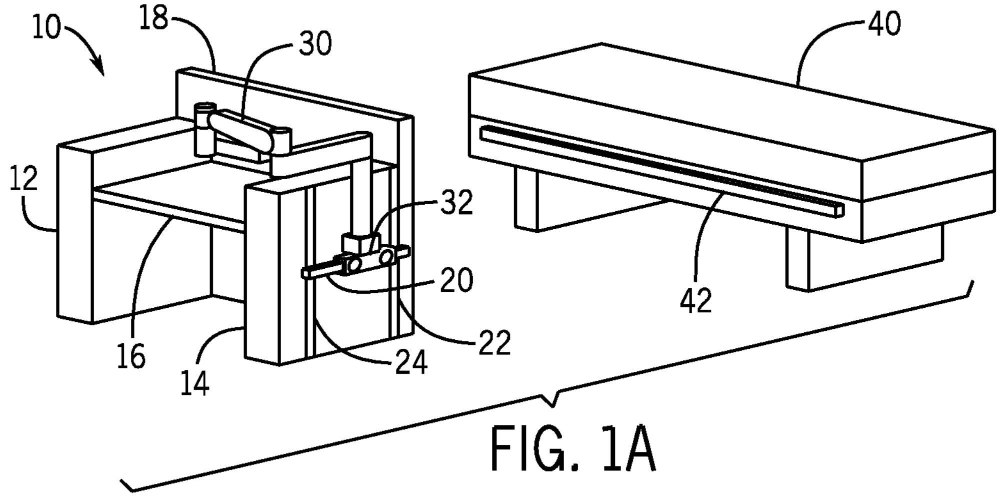
FIG. 1A is a perspective view of a radiation shielding cockpit with an articulated robotic arm attached and an adjacent patient table.

Referring to FIG. 1A, a radiation shielding cockpit 10 is shown with a left side wall 12, a right side wall 14, a horizontal work table 16 and a front wall 18. Attached to the right side wall 14 is a mounting rail 20. This attachment is via right vertical rail 22 and left vertical rail 24, both of which are attached to the right wall 20. An articulated robotic arm 30 is attached to the mounting rail 20 via an articulated robotic arm mounting bracket 32. The articulated robotic arm 30 is in a stored position with most of its structure lying above the cockpit work table 16. Adjacent the radiation shielding cockpit 10 is a patient rail 40 which has an articulated robotic arm mounting bracket 42. In one embodiment to put the system into use and perform a procedure the articulated robotic arm 30 is removed from the mounting rail 20 and attached to the patient table mounting rail 42. After a procedure is completed the articulated robotic arm 30 may be removed from the patient table mounting rail 42 and attached to the cockpit mounting rail 20 thus facilitating its storage out of the way of medical personal who perform their functions such as transport of the patient and preparing the patient table to receive a patient in the close vicinity of the patient table 40.

Figure 1B:
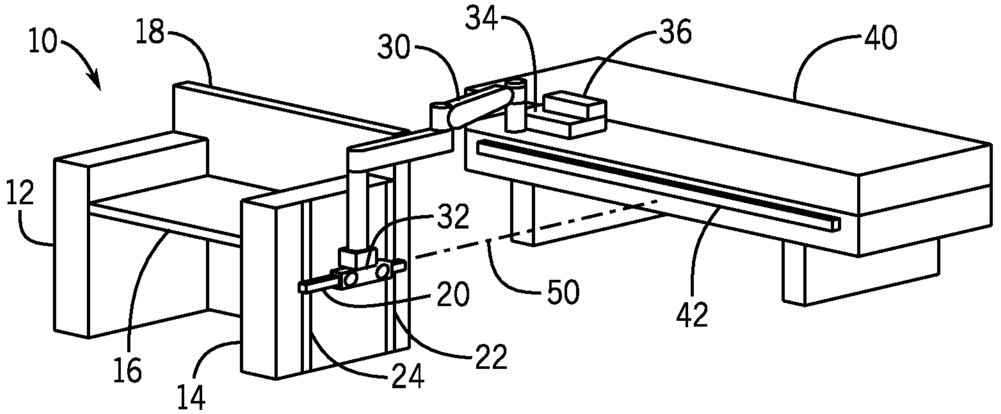
FIG. 1B is a perspective view of a radiation shielding cockpit with an articulated robotic arm attached and deployed above an adjacent patient table.

Referring to FIG. 1B, a similar arrangement to that of FIG. 1B is shown with the item numbers having the same meaning However, in this case the articulated robotic arm 30 is dynamically mounted to the radiation shielding cockpit 10. The articulated robotic arm 30 includes a mechanism which allows it to track any movements of the patient table 40, particularly in the xy or horizontal plane, and deploy its drive motor mounting base 34 and its attached cassette 36 in a proper orientation to the patient table 40 and therefore the patient (Not illustrated). The tracking mechanism of the articulated robotic arm 30 may be instructed by a wireless positioning signal 50. In this embodiment the patient table mounting rail 42 is not used.

Articulated robotic arm 30 may also be controlled in the z direction and automatically adjusted in the vertical z direction by a controller to ensure that the height of the robotic arm 30 is constant with respect to the patient table 40 or patient. This would allow for a constant positioning of a robotic catheter drive with the patient. If the patient moved for example on the table the robotic arm could automatically adjust so that the guide wire or catheter does not move relative to the patient in an undesirable manner.

Although, not shown in FIG. 1A or 1B cockpit 10 may include radiation shields that extend over the walls of the cockpit. In one embodiment, two of the walls have a transparent radiation shield extending upward from the walls, while the third wall remains free of a shield so that the robotic arm may be rotated into the center portion of the cockpit when not in use. Alternatively, a shield may be located on the third wall and removable or may be lowered to allow at least a portion of the robotic arm to swing into the center area of the cockpit when it is desired to store the robotic arm when not in use.

While only certain features of the invention have been illustrated and described herein, many modifications and changes will occur to those skilled in the art. It is, therefore, to be understood that the appended claims are intended to cover all such modifications and changes as fall within the true spirit of the invention. A number of features are disclosed herein.

These features may combined in multiple combinations such that features may be used alone or in any combination with any of the other features.

What is claimed is:

1. A radiation shielded cockpit comprising:

a radiation blocking material which creates a semi-enclosed work space;

a structure for receiving and supporting an articulated robot arm; and an articulated robot arm that engages the supporting structure in a readily removable manner; a mechanism for tracking the horizontal movement of a patient table and moving the robot arm in accordance with that tracking; and robotic catheter drive operatively supported by the articulated robot arm.

2. The shielded cockpit of claim 1 wherein the receiving and supporting structure is located on the exterior of the cockpit.

3. The shielded cockpit of claim 1 wherein the cockpit comprises intersecting walls.

4. The shielded cockpit of claim 3 wherein the walls are essentially vertical.

5. The shielded cockpit of claim 4 wherein there are three walls that intersect at essentially right angles.

6. The shielded cockpit of claim 5 wherein one of the side walls carries the receiving and supporting structure.

7. The shielded cockpit of claim 6 wherein the receiving and supporting structure comprises a bracket attached the side wall.

8. The shielded cockpit of claim 7 wherein the bracket is attached to the side wall by two parallel vertical rails that are directly affixed to the side wall.

9. The shielded cockpit of claim 5 wherein an essentially horizontal worktable is affixed to the three walls.

10. The shielded cockpit of claim 1 wherein the enclosed workspace contains an essentially horizontal worktable.

11. The shielded cockpit of claim 10 wherein when the articulated robot arm engages the supporting structure most of the arm lies above the worktable.

12. A radiation shielded cockpit comprising:

a configuration of radiation blocking materials which creates a semi-enclosed work space;

a structure for receiving and supporting an articulated robot arm; and an articulated robot arm that engages the supporting structure and has a mechanism for tracking the horizontal movement of a patient table and moving the robot arm in accordance with that tracking; and a robotic catheter drive operatively supported by the articulated robot arm.

13. The shielded cockpit of claim 12 wherein the robot arm carries a cassette attached to a drive motor mounting base.

14. The shielded cockpit of claim 13 wherein the robot arm is moved in the vertical direction by a controller in accordance with the vertical position of the patient table or a patient on the table.

15. The shielded cockpit of claim 14 wherein the tracking mechanism and the controller act to keep the cassette in a constant position relative to the patient.

16. The shielded cockpit of claim 12 wherein the mechanism for tracking the horizontal movement of the patient table receives a wireless positioning signal.

17. The shielded cockpit of claim 12 wherein the receiving and supporting structure is located on the exterior of the cockpit.

18. The shielded cockpit of claim 12 wherein enclosed workspace contains an essentially horizontal worktable and when the articulated robot arm engages the supporting structure most of the arm lies above the worktable.

19. A process for storing an articulated robot arm comprising:

providing:

the articulated robot arm; a robotic catheter drive operatively supported by the articulated robot arm;

a configuration of radiation blocking materials which creates a semi-enclosed work space; and a structure that is attached to the configuration of radiation blocking materials and engages the articulated robot arm in a readily removable manner and when so engaged supports the arm; and causing the structure to engage the robot arm in a readily removable manner.

20. The process of claim 19 wherein the articulated robot arm has a mechanism for tracking the horizontal movement of a patient table and moving the robot arm in accordance with that tracking.

* * * * *